(12) United States Patent
Boettger et al.

(10) Patent No.: US 9,327,080 B2
(45) Date of Patent: May 3, 2016

(54) PISTON FOR A MEDICAL HOLLOW BODY, AND MEDICAL HOLLOW BODIES

(75) Inventors: Frank Boettger, Ravensburg (DE); Benjamin Boebst, Mittelbiberach (DE)

(73) Assignee: ARZNEIMITTEL GMBH APOTHEKER VETTER & CO. RAVENSBURG, Ravensburg (DE)

( * ) Notice: Subject to any disclaimer, the term of this patent is extended or adjusted under 35 U.S.C. 154(b) by 123 days.

(21) Appl. No.: 13/377,927

(22) PCT Filed: Jun. 9, 2010

(86) PCT No.: PCT/EP2010/003449
§ 371 (c)(1),
(2), (4) Date: Dec. 13, 2011

(87) PCT Pub. No.: WO2010/145771
PCT Pub. Date: Dec. 23, 2010

(65) Prior Publication Data
US 2012/0101453 A1    Apr. 26, 2012

(30) Foreign Application Priority Data
Jun. 18, 2009   (DE) .......................... 10 2009 025 375

(51) Int. Cl.
*A61M 5/315*    (2006.01)
*A61M 5/20*    (2006.01)

(52) U.S. Cl.
CPC ......... *A61M 5/31513* (2013.01); *A61M 5/2053* (2013.01)

(58) Field of Classification Search
CPC ........................ A61M 5/31513; A61M 5/2053
USPC ........................................... 604/218, 226, 230
See application file for complete search history.

(56) References Cited

U.S. PATENT DOCUMENTS

| | | | |
|---|---|---|---|
| 684,840 A | | 1/1901 | Douds |
| 718,979 A | | 1/1903 | Campbell |
| 1,450,016 A | * | 3/1923 | Bruce ........................... 604/230 |
| 1,718,599 A | * | 6/1929 | Smith ........................... 604/234 |
| 1,949,612 A | | 3/1934 | Mattair et al. |
| 2,545,017 A | | 3/1951 | Billingsley |
| 3,327,904 A | | 6/1967 | Goda et al. |
| 3,659,749 A | * | 5/1972 | Schwartz ....................... 222/129 |
| 4,074,715 A | * | 2/1978 | Geiger ........................... 604/230 |
| 5,353,691 A | * | 10/1994 | Haber et al. .................... 92/159 |
| 5,743,890 A | | 4/1998 | Hjertman et al. |
| 6,090,081 A | * | 7/2000 | Sudo et al. ..................... 604/230 |

(Continued)

FOREIGN PATENT DOCUMENTS

EP        1317937 A1    6/2003

OTHER PUBLICATIONS

International Search Report and Written Opinion of the ISA for PCT/EP2010/003449, ISA/EP, Rijswijk, NL, mailed Jan. 21, 2011.

(Continued)

*Primary Examiner* — Theodore Stigell
(74) *Attorney, Agent, or Firm* — Harness, Dickey & Pierce, P.L.C.

(57) ABSTRACT

A piston for a medical hollow body such as a syringe or a carpule includes at least one sliding surface for contact with the hollow body. The piston has at least one receiving area in which a lubricant can be received, and at least one dispensing mechanism for dispensing the at least one lubricant from the at least one receiving area to the at least one sliding surface.

6 Claims, 8 Drawing Sheets

(56) References Cited

U.S. PATENT DOCUMENTS

| | | | |
|---|---|---|---|
| 6,093,175 A * | 7/2000 | Gyure et al. | 604/230 |
| 6,142,977 A * | 11/2000 | Kolberg et al. | 604/218 |
| 6,960,195 B2 * | 11/2005 | Heinz et al. | 604/222 |
| 8,167,850 B2 * | 5/2012 | Hoffmann et al. | 604/222 |
| 8,226,630 B2 * | 7/2012 | Ackerman et al. | 604/500 |
| 2003/0168480 A1 | 9/2003 | Kim | |
| 2004/0084852 A1 | 5/2004 | Tachikawa et al. | |
| 2005/0212222 A1 * | 9/2005 | Tachikawa et al. | 277/628 |

OTHER PUBLICATIONS

First Office Action regarding Japan Application No. 2012-515376 mailed Feb. 12, 2014. Translation provided by Suzuye & Suzuye.

Notice of Allowance in Russian Application No. 2012101622 dated Jun. 2, 2014.

* cited by examiner

PISTON FOR A MEDICAL HOLLOW BODY, AND MEDICAL HOLLOW BODIES

CROSS-REFERENCE TO RELATED APPLICATIONS

This application is a 371 U.S. National Stage of International Application No. PCT/EP2010/003449, filed Jun. 9, 2010, which claims priority to German Patent Application No. 102009025375.0, filed Jun. 18, 2009. The disclosures of the above applications are incorporated herein by reference.

FIELD

The invention relates to a piston for a medical hollow body according to the preamble of the claim 1. It further relates to a piston for a medical hollow body according to the preamble of the claim 14, and to a medical hollow body according to the preamble of the claim 18.

BACKGROUND

Pistons for medical hollow bodies, in particular syringes or carpules, are known. They typically have a substantially cylindrical shape and can be introduced in a likewise substantially cylindrical interior of a medical hollow body. On an outer surface shell, such a piston has at least one sliding surface with which said piston rests against an inner surface shell of an interior of the hollow body. Preferably, the piston comprises a material, at least in the area of this sliding surface, which is more elastic than the material of which the medical hollow body is made. Moreover, the outer diameter of the piston is preferably slightly larger than the inner diameter of the medical hollow body. If the piston is introduced into the medical hollow body in such a manner that the longitudinal axes of the piston and the hollow body are aligned with each other, this results in an at least slight compression of the piston material in the area of the at least one sliding surface so that a sealing effect is established here. Thus, the piston sealingly closes the interior of the hollow body. At the same time, a displacement of the piston within the hollow body is possible, wherein the piston slides with its at least one sliding surface on the inner surface shell of the hollow body. This sliding movement of the piston can be used to optionally expel or draw in a medium, for example, a pharmaceutical substance or a sample, through an opening of the hollow body which—viewed in the axial direction of the hollow body—is located opposite to the piston.

Known pistons for medical hollow bodies comprise materials which, in connection with the material of which the hollow body is made, have high coefficients of static and sliding friction in the area of the at least one sliding surface of the piston when the latter rests against the hollow body so that a displacement of the piston relative to the hollow body with an acceptable exertion of force is not possible without further measures. Depending on the elasticity of the piston, the latter can deform when axial forces are introduced, which results in an increase of the static friction in the area of the at least one sliding surface. An increase of the axial forces results in that the friction forces counteracting a displacement of the piston are intensified so that finally a blocking of the piston occurs and therefore the piston can no longer be displaced. In the case of a further increase of the axial forces, this can result in a destruction of the piston.

In order to allow a displacement of the piston with acceptable force exertion while avoiding a blocking, it is known to coat the inner surface shell with a lubricant so that the piston can slide during its displacement in the hollow body with its at least one sliding surface on a lubricating film formed by the lubricant. Typically, silicone, silicone oil, and/or silicone oil emulsions are used as a lubricant.

In order to allow a displacement of the piston along the entire axial extension of the interior of the hollow body, the entire inner surface shell of the latter has to be coated with the lubricant. This is usually carried out prior to introducing the piston into the hollow body and in particular prior to filling the hollow body with a pharmaceutical substance. Hereby, the pharmaceutical substance is in contact with the lubricant during storage of the prefilled hollow body. The disadvantage of this is that in particular in the case of biotechnologically produced, sensitive pharmaceutical substances, interactions with the lubricant can take place. In particular, it is known that silicone oil can result in instability of active ingredients which comprise proteins and/or peptides. For example, aggregate formation or precipitation can take place. Also, the potentially forming aggregates are suspected to trigger a series of undesirable immune reactions. The coating of the interior of a medical hollow body which comprises a substance intended to be injected into a patient thus can result not only in a reduction of the efficacy, but can in fact have negative consequences for the health of the patient to whom the injection is administered.

SUMMARY

It is therefore an object of the invention to provide a piston for a medical hollow body, wherein the friction of the sliding surface on an inner surface of a medical hollow body is reduced so that coating the interior of the hollow body with a lubricant can be dispensed with, at least prior to carrying out an injection.

The object is achieved by a piston with the feature of the claim 1. The piston is characterized by at least one receiving area, wherein at least one lubricant can be received in said receiving area. Furthermore, at least one dispensing means is provided by means of which the at least one lubricant can be dispensed from the at least one receiving area to the at least one sliding surface of the piston. Thus, the piston itself comprises the lubricant required for its displacement and distributes it preferably with the aid of the dispensing means during its displacement in the area of the at least one sliding surface so that a lubricating film is created here on which the piston can slide. In this manner, the lubricating film is generated at any time of the displacement of the piston precisely at those places where the piston is situated. Hereby, a prior coating of the interior of the hollow body with a lubricant is not required so that in particular during storage of the hollow body filled with a pharmaceutical substance, no contact of the pharmaceutical substance with the lubricant is possible. Instabilities of the pharmaceutical substances caused by the lubricant can thus be avoided.

Particularly preferred is an exemplary embodiment of the piston in which in a first state, no lubricant can be dispensed from the at least one receiving area, wherein in a second state of the piston, lubricant can be dispensed by the at least one dispensing means to the at least one sliding surface. Thus, if the piston is in its first state, which typically is the case during storage of the hollow body prefilled with the pharmaceutical substance and sealed with the piston, no lubricant can be dispensed from the receiving area so that in particular no contact of the lubricant with the pharmaceutical substance is possible. The second state addresses a displacement of the piston, thus, for example, an injection. In this state, lubricant is to be dispensed to the at least one sliding surface so as to enable a piston displacement with a friction as low as possible.

Preferred is an exemplary embodiment in which the piston is unpressurized in the first state and is subjected to a pressure in the second state. As long as the piston is not pressurized, the lubricant remains in the receiving area, whereas the pressure exerted on the piston in the second state effects, on the one hand, a release of the lubricant and, on the other, a displacement of the piston.

Further advantageous configurations arise from the subclaims.

The object underlying the invention is achieved by a piston with the features of the claim 14. Said piston is characterized in that the piston, at least in the area of the at least sliding surface, comprises a smooth nonpolar material. Such a material gives the piston a low static friction compared to known pistons and also a reduced sliding friction in contact with the inner surface shell of the hollow body. In this case too, coating of the inner surface shell of the hollow body with a lubricant can be eliminated without causing the need that excessive forces have to be applied for displacing the piston in the hollow body. In this exemplary embodiment, no coating of the inner surface shell with the lubricant takes place during the displacement of the piston. Thus, a lubricant is advantageously completely dispensed with.

Particularly preferred is an exemplary embodiment in which the smooth nonpolar material comprises PTFE and preferably consists of PTFE. This material known under the trade name Teflon has particularly good sliding properties and, furthermore, is available at low cost.

Further advantageous configurations arise from the subclaims.

Moreover, it is an object of the invention to provide a medical hollow body wherein coating an interior or at least an inner surface shell with a lubricant in particular prior to introducing a pharmaceutical substance or prior to closing the hollow body, respectively, can be dispensed with. In this manner it is avoided that a pharmaceutical substance stored in the hollow body comes into contact with a lubricant resulting in the mentioned disadvantageous consequences.

The object is achieved by a medical hollow body with the features of the claim 18.

The medical hollow body, in particular a syringe or carpule, comprises at least one piston which can be displaced in an interior of the hollow body along the longitudinal axis of the same. Said hollow body is characterized in that the piston is formed according to any one of the claims 1 to 13 or according to any one of the claims 14 to 17. Thus, the piston has at least one receiving area with lubricant and at least one corresponding dispensing means, or it comprises, at least in the area of its one sliding surface, a smooth nonpolar material.

Particularly preferred is an exemplary embodiment of the medical hollow body in which, in addition, a device is provided by means of which pressure forces can be exerted on the at least one piston by a chemical reaction. In order to effect a displacement of the piston, thus, a chemical reaction can be initiated by means of which gases can be released as reaction products, wherein an overpressure is created that drives the piston. In the case of an adequately formed piston, the overpressure can be used at the same time to expel the lubricant provided in the receiving area and to dispense it via the at least one dispensing means to the at least one sliding surface.

Finally, also preferred is a medical hollow body which comprises a piston rod by means of which pressure forces can be exerted on the at least one piston. Thus, the medical hollow body, for example a syringe or carpule, except for the piston, can be formed in a conventional manner wherein via the piston rod, manually or with the aid of a machine-driven syringe feed, forces can be introduced into the piston which effect the displacement of the piston and/or, if necessary, an expulsion of the lubricant comprised by the receiving area.

BRIEF DESCRIPTION OF THE DRAWINGS

The invention is explained in more detail below by means of the drawing. In the figures.

DETAILED DESCRIPTION

Figure 1:
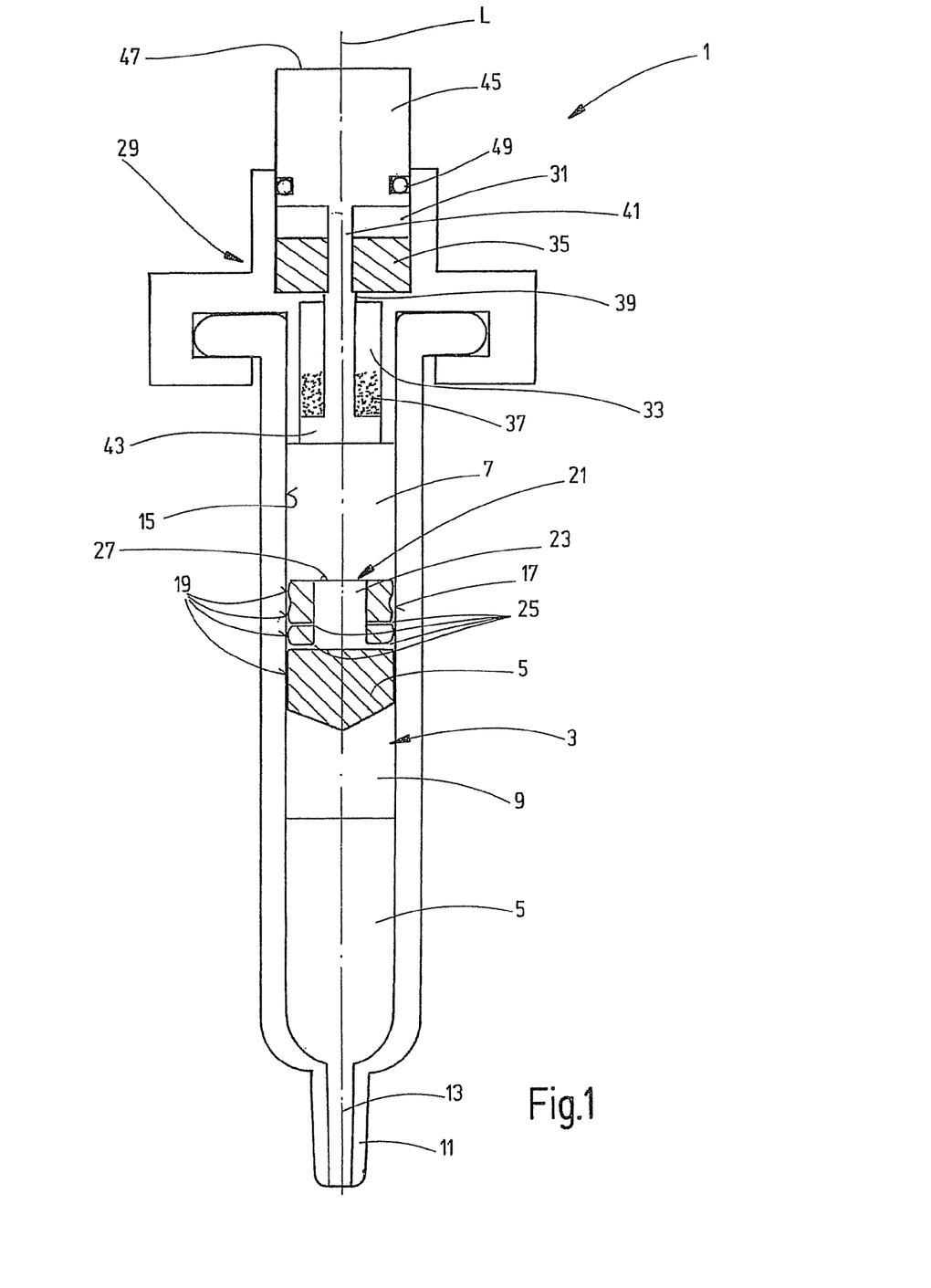
FIG. 1 shows a schematic view of a first exemplary embodiment of a medical hollow body with a first exemplary embodiment of a piston according to claim 1.

FIG. 1 shows a first exemplary embodiment of a medical hollow body 1 which is formed here as a syringe. In other exemplary embodiments, which are not illustrated, the hollow body can also be formed as a carpule, a double- or multi-chamber syringe or carpule, a pen, an auto-injector, or in any other suitable manner. The hollow body 1 is formed substantially cylindrically and comprises an interior 3 in which a likewise substantially cylindrical piston 5 can be displaced along the coinciding longitudinal axes L of the piston 5 and the hollow body 1. The piston 5 divides the interior 3 into an upper subspace 7 and a lower subspace 9. In the lower subspace 9, preferably, a pharmaceutical substance S is arranged which can be dispensed through a channel 13, which is formed in a connection piece 11 and is in fluid communication with the lower subspace 9, when the piston 5 is displaced downward along the axis L, thus toward the connection piece 11.

The interior 3 encloses a substantially cylindrical inner surface shell 15 of the hollow body 1. The piston 5 has a likewise cylindrical outer surface shell 17 which in the illustrated exemplary embodiment—in a cross-sectional view—has a quasi wavelike shape so that—viewed in the axial direction—areas having a larger diameter alternate with areas having a smaller diameter. At least in the area of the outer surface shell 17, the piston 5 preferably comprises a material which is more elastic than the material of which at least the area of the hollow body 1 which comprises the inner surface shell 15 is made. Preferably, the areas of the surface shell 17 having a larger diameter are formed such that their diameter is slightly larger than the inner diameter of the interior 3.

If, in this case, the piston 5 is introduced into the interior 3, the areas of the surface shell 17 having a larger diameter are compressed so that sliding surfaces 19 are formed here with which the piston 5 rests against the hollow body 1. In another exemplary embodiment, which is not illustrated, the outer surface shell 17 can be a cylinder surface, wherein in this case, the outer diameter of said cylinder is preferably slightly larger than the inner diameter of the interior 3. In this case, the entire outer surface shell 17 of the piston 5 forms a single sliding surface 19.

During a displacement of the piston 5 in the hollow body 1, the at least one sliding surface 19 slides on the inner surface shell 15 of the interior 3.

The piston 5 has a receiving area 21 which comprises a lubricant. In other exemplary embodiments, which are not illustrated, more than one receiving area 1 can be provided. For example, the receiving area 21 can be divided so that a plurality of receiving areas are created. Also, the piston 5 can comprise separate receiving areas 21.

The receiving area 21 comprises here a hollow space 23 which serves as reservoir for the lubricant.

Preferably, silicone, a silicone oil, or a silicone oil emulsion can be used as a lubricant. A mixture of these substances is also possible. If different receiving areas are provided, said receiving areas are preferably able to receive different lubricants so that a large variation is possible here.

At least one dispensing means is provided by means of which the at least one lubricant can be dispensed from the at least one receiving area 21 to the at least one sliding surface 19. The dispensing means comprises here channels 25 which connect the hollow space 23 to the outer surface shell 17 and open out therein so that said channels run in particular from the receiving area 21 to the sliding surfaces 19. Thus, lubricant can flow in the channels 25. In another exemplary embodiment, which is not illustrated, it is also possible that only a single channel 25 is provided. However, it is preferred that a plurality of channels 25 intersect the surface shell 17 along the circumference of the same preferably with the same angular partition so that the lubricant—viewed in the circumferential direction—can be distributed very evenly on the sliding surfaces 19. In the illustrated exemplary embodiment, two annular areas of the surface shell 17 are provided which are offset to one another in the axial direction and are intersected by channels 25. Depending on the longitudinal expansion of the piston 5, more or fewer of such preferably annular areas can be provided, whereby the lubricant can be evenly distributed also in the axial direction over the one sliding surface 19 or the different sliding surfaces 19. Of course, in the case of other exemplary embodiments, which are not illustrated, a less symmetrical distribution of channels 25 is also possible.

FIG. 1 illustrates the piston 5 in a first state in which no lubricant can be dispensed from the at least one receiving area. The hollow space 23 does not penetrate the entire piston 5 along the piston's axial extension but extends viewed in the axial direction—from the piston's 5 end opposing the connection piece 11 only to approximately the middle of the piston. The hollow space's 23 end which—viewed in the axial direction—is located opposite to the connection piece 11 is closed here by a preferably liquid-tight diaphragm 27 which prevents the lubricant from leaking in this area. In the illustrated state of the piston, no lubricant can escape from the channels 25 because they open out in very small areas which are arranged between the sliding surfaces 19 and can receive only a minimal volume of lubricant. However, it is essential that in the illustrated state, the piston 5 and in particular the hollow space 23 are unpressurized so that a low-pressure would be generated in the upper area of the hollow space 23 in the event that lubricant would escape from the channels 25. Thus, the overall conclusion is that in this state, no lubricant can be dispensed from the at least receiving area 21.

The diaphragm 27 closes the hollow space 23, thus also the receiving area 21 in the upper area of the latter. If a plurality of receiving areas 21 are provided, it is possible to close these receiving areas by a plurality of diaphragms at least in certain areas so that each receiving area 21 is associated with one diaphragm. In other exemplary embodiments, it is also possible that one receiving area is associated with a plurality of diaphragms which close said receiving areas in certain areas. It is essential that the piston 5 comprises at least one diaphragm 27 which closes the at least one receiving area 21 at least in certain areas.

In one preferred exemplary embodiment, the piston 5 comprises an elastomer. Particularly preferred, the piston 5 comprises the elastomer in the area of its outer surface shell 17 and particularly in the area of the at least one sliding surface 19. Thus, the elasticity of the piston 5 can be ensured in this area, which allows a tight surface contact of the at least one sliding surface 19 on the hollow body 1. Also, the piston 5 can preferably consist of an elastomer. Thereby, the piston is easier to produce than if the piston comprises a plurality of materials and, for example, comprises elastomer only in outer areas.

In order to reduce the static friction and also the sliding friction of the piston 5 beyond the effect achieved by the lubricant, the piston 5 can preferably comprise PTFE, particularly preferred consists of PTFE. If the piston 5 comprises PTFE only in certain areas, this is preferably provided in the area of the outer surface shell 17 and in particular in the area of the at least one sliding surface 19. Providing the piston 5 with PTFE at least in the area of the at least one sliding surface 19 results in that the static friction and the sliding friction are already significantly reduced without additional lubrication. Therefore, together with the lubricant, a displaceability of the piston 5 is achieved which requires particularly little force.

In the illustrated exemplary embodiment, the medical hollow body 1 comprises a device 29 by means of which pressure forces can be exerted on the piston 5 by a chemical reaction. For this purpose, the device 29 comprises a first chamber 31 and a second chamber 33. In said chambers 31, 33, substances are disposed which, as long as they are spatially separated from each other, are stable at least over a typical storage period of a prefilled hollow body 1. However, if they are brought into contact with each other, they can—if the case may be, after overcoming an activation barrier—undergo a chemical reaction with each other wherein at least one gas is released. A substance 35 is disposed in the first chamber 31 and a substance 37 is disposed in the second chamber 33. The second substance 37 can comprise, for example, sodium hydrogen carbonate, wherein the first substance 35 preferably comprises an organic acid, for example citric acid, or a mineral acid. In the case of a reaction of the acid with the sodium hydrogen carbonate, carbon dioxide is released so that a gas pressure can be built up. In principal it is sufficient if in one of the chambers 31, 33, a metastable pure substance is present which, upon overcoming an activation barrier, is degradable and releases a gas during its degradation. In the other chamber, a catalyst can be arranged which, for triggering the chemical reaction, is brought into contact with the pure substance. In yet another exemplary embodiment, it is also possible that the two substances 35, 37 react with each other only after overcoming an activation barrier.

For this, in addition to one of the two substances 35, 37, a catalyst can be arranged in one of the two chambers 31, 33, wherein said catalyst become fully effective not until the two substances 35, 37 are brought into contact. In another preferred exemplary embodiment, a starter mechanism can be integrated in the device 29, which starter mechanism overcomes the activation barrier thermally, electrochemically, or in a different suitable manner known per se. For this purpose, heating devices or electrodes can be provided, for example. Once the activation barrier of a metastable pure substance is overcome in a thermal, electrochemical or other physical manner, it is sufficient to provide a single chamber which comprises the pure substance and, in addition, a suitable starter mechanism for the degradation of said pure substance.

If two substances 35, 37 are provided which react with each other while developing gas when brought into contact, these substances have to be stored in the chambers 31, 33 separated from each other prior to actuating the device 29. For this, a separating element 39 is provided which, in the illustrated exemplary embodiment, is formed as a portion of a rod 41 of a closure element 43.

In other exemplary embodiments, which are not illustrated, the separating element can be formed as a pierceable septum, a tearable or breakable diaphragm, a solid breaking element, or in another suitable manner.

The closure element 43 closes the second chamber 33 tightly with respect to the upper subspace 7 so that the substance 37 cannot leak into the latter. The separating element 39 separates the chambers 31, 33 from each other so that the substances 35, 37 cannot get into contact with each other. An actuating element 45 is provided which serves for bringing the chambers 31, 33 into fluid communication with each other so that the substances 35 and 37 come into contact and can react with each other. Depending on the exemplary embodiment of the separating element 39, the actuating element 45 can be formed as hollow needle, solid plunger or in another suitable manner. In the illustrated exemplary embodiment, the actuating element 45 has at its upper end an actuating area 47 into which pressure forces can be introduced in the axial direction. Said actuating element also comprises a seal 49 which is formed here as an O-ring arranged in an annular groove. The actuating element 45 is connected to the rod 41 and thus also to the closure element 43 and the separating element 39 so that these elements, upon introducing axial forces, are displaced together downward into the actuating area 47, thus toward the connection piece 11.

Figure 2:
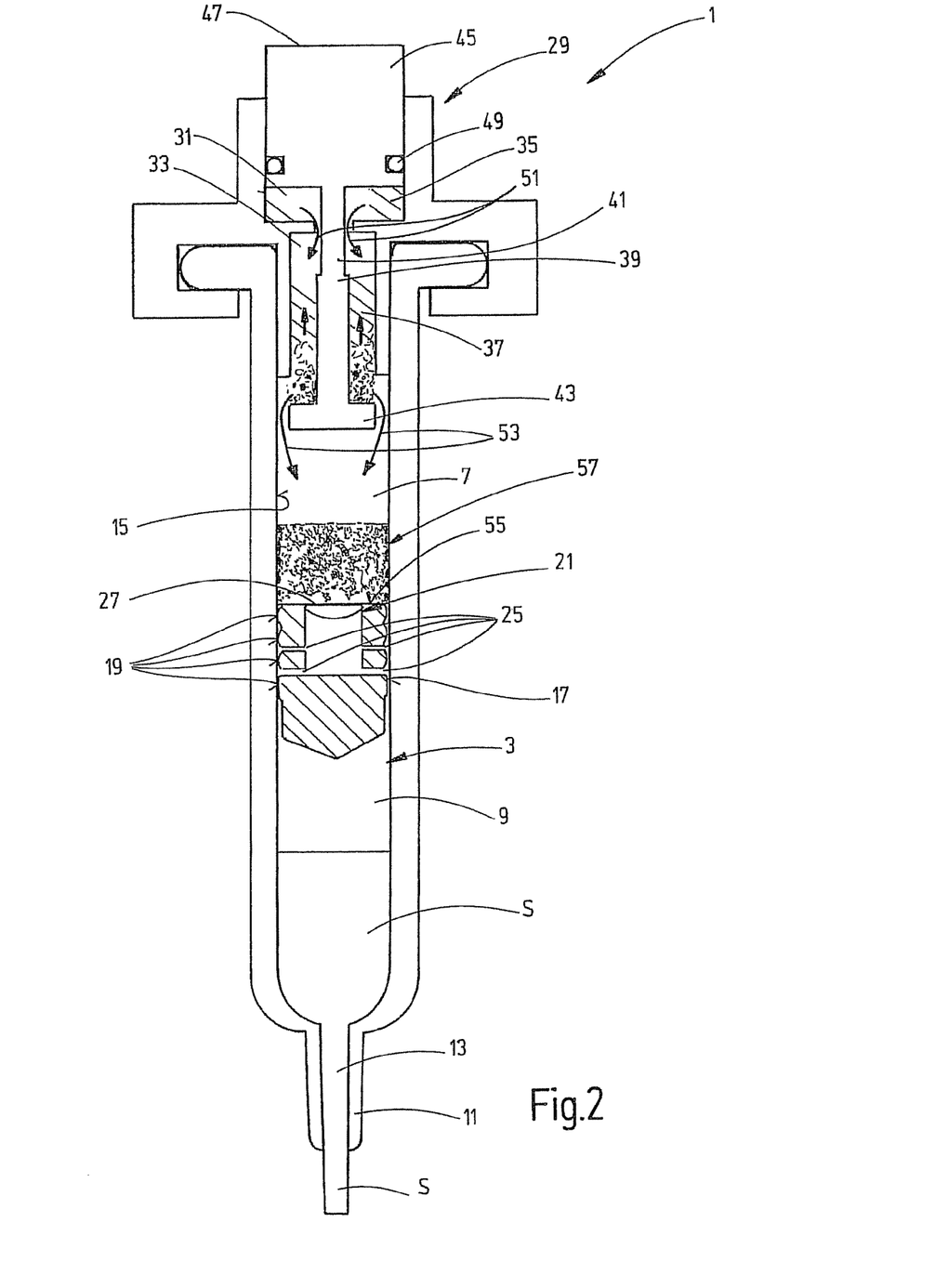
FIG. 2 shows another schematic view of the medical hollow body according to FIG. 1 during a displacement of the piston.

FIG. 2 shows the exemplary embodiment according to FIG. 1 with the device 29 being activated and in particular during displacement of the piston of the piston 5. Identical and functionally identical elements are indicated by the same reference numbers so that in this respect, reference is made to the preceding description. It becomes obvious in FIG. 2 that by displacing the actuating element 45 and the elements connected thereto in the downward direction, on the one hand, a fluid communication between the chambers 31, 33 and, on the other, a fluid communication between the chamber 33 and the upper subspace 7 is created. Hereby, the substance 35 flows along the arrows 51 from the first chamber 31 into the second chamber 33. There, said substance comes into contact with the substance 37 so that it can react with the same. At the same time, the substance 37 or, respectively, a mixture of the substances 35, 37 leaves the chamber 37 along the arrows 53 and gets into the upper subspace 7. During the reaction of the substances 35, 37, at least one gas is released for which a limited volume is available which is defined by the chambers 31, 33 and the upper subspace 7.

The at least one released gas preferably involves a chemically non-aggressive, non-toxic gas, particularly preferred an inert gas. The continuous gas formation during the reaction results in an increase of the pressure in the volume available for the gas, wherein the pressure acts on a surface 55 of the piston 5, which surface faces toward the upper subspace 7, and acts in particular also on the diaphragm 27. In a preferred exemplary embodiment, which is not illustrated, the diaphragm 27 can be elastic so that due to pressure forces acting on the diaphragm, the latter is curved into the hollow space 23. Thereby, the pressure forces are transferred to the lubricant disposed in the receiving area 21, wherein said lubricant is dispensed via the channels 25, which act as dispensing means, to the sliding surface 19. In this manner, a lubricating film is formed between the at least one sliding surface 19 and the inner surface shell 15, whereby the friction forces prevailing therein are reduced and the piston 5 can be displaced more easily. The pressure forces acting on the surface 55 result at the same time in a displacement of the piston 5 downward onto the connection piece 11 so that the subspace 7 becomes larger while the subspace 9 becomes smaller. Hereby, the substance S disposed in the lower subspace 9 is expelled through the channel 13 in the connection piece 11, which is illustrated schematically here. Thus, the substance S can be taken from the hollow body 1; preferably, an injection can take place if the hollow body is formed as a syringe, a carpule, or other injection device, wherein a non-illustrated injection needle is coupled with the connection piece 11.

In the illustrated exemplary embodiment, however, the diaphragm 27 is not elastic but is permeable so that the at least one gas released during the reaction can permeate through the diaphragm 27 and can enter into the hollow space 23. Thus, pressure equalization between the upper subspace 7 and the hollow space 23 takes place which is why the diaphragm 27 does not deform. At the same time, the pressure forces acting in the subspace 7 are transferred to the lubricant disposed in the receiving area 21 so that said lubricant can be dispensed via the channels 25 to the at least one sliding surface 19. Moreover, due to the pressure forces acting on the surface 55, the piston 5 is displaced downward. Thereby, a lubricating film remaining behind the piston 5 is generated on the inner surface shell 15 and is illustrated here as a dotted area. Thus, after a displacement of the piston 5, the lubricant adheres at least partially on the inner surface shell 15.

In another, non-illustrated exemplary embodiment, the piston can also consist of a squashable or squeezable material which preferably has a number of pores in which the lubricant is disposed. Thus, the pores form receiving areas in which the lubricant can be received. If pressure forces are introduced into the piston 5, the latter deforms at least in certain areas resulting in a reduction of the volume of the individual pores, thus of the receiving areas. Hereby, the lubricant can be dispensed from the pores so that the pores disposed on the surface shell 17 of the piston, in connection with the outer and the inner pores and the channels interconnecting said pores, act also as a dispensing means, wherein the lubricant can be dispensed here from the receiving areas to the at least one sliding surface. Thus, in this case, the piston 5 is quasi squeezed or squashed by the pressure forces, wherein lubricant is dispensed and wherein, at the same time, the piston 5 is displaced by the pressure forces acting on its surface 55.

Overall, it becomes apparent that the piston in FIG. 2 is illustrated in a second state in which lubricant can be dispensed through the at least one dispensing means to the at least one sliding surface. In the illustrated exemplary embodiment, the piston 5 is pressurized in the second state, wherein the pressure forces are transferred to the lubricant and expel the same from the receiving area so that it can be dispensed to the at least one sliding surface 19.

As already mentioned, the diaphragm 27 can be elastic, but also permeable for gases. Of course, it is also possible in other preferred exemplary embodiments to configure the diaphragm 27 to be elastic and also permeable for gases.

Figure 3:
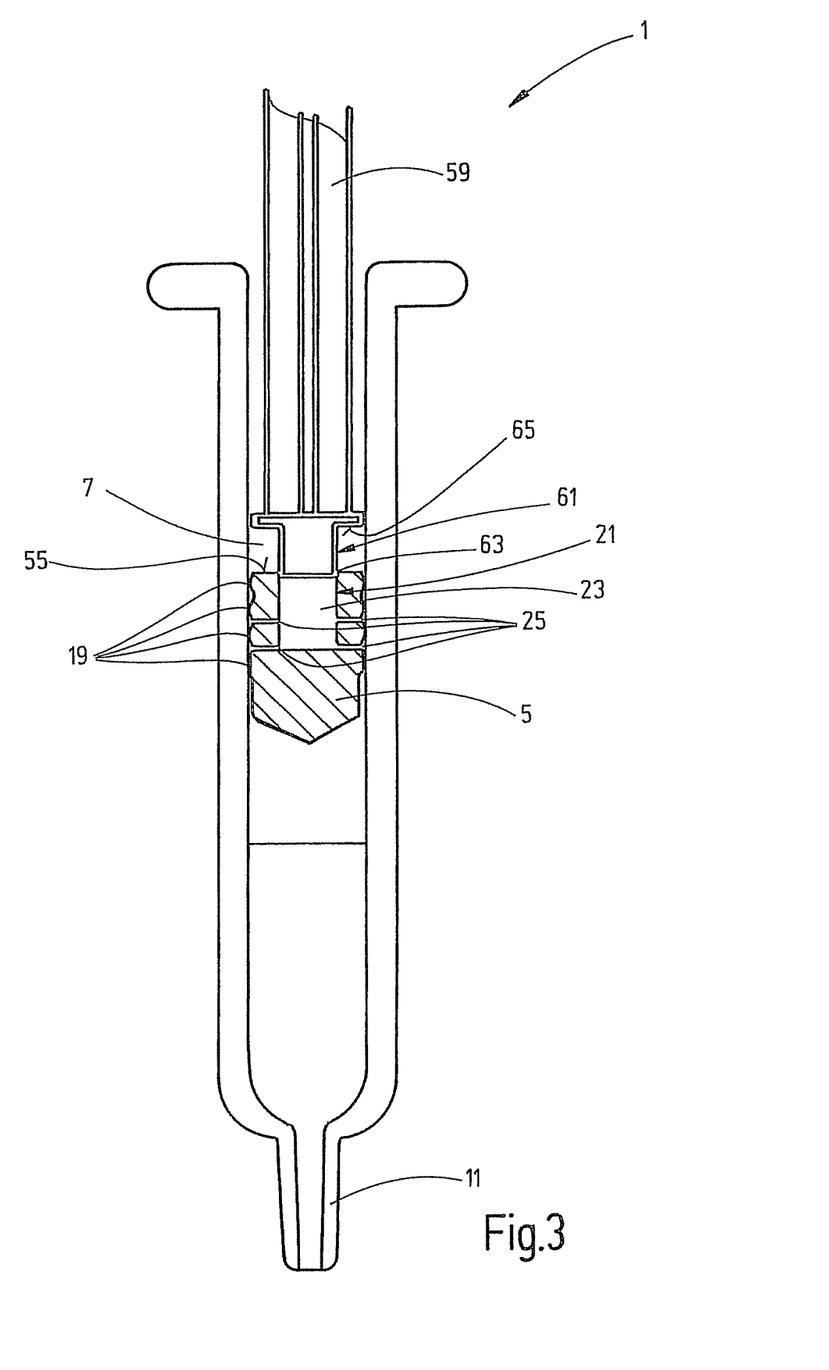
FIG. 3 shows a schematic view of a second exemplary embodiment of a medical hollow body with a further exemplary embodiment of a piston according to claim 1.

FIG. 3 shows a second exemplary embodiment of a hollow body 1 in which a further exemplary embodiment of a piston 5 is arranged. Identical and functionally identical elements are indicated by the same reference numbers so that in this respect, reference is made to the preceding description. In contrast to the exemplary embodiment of a medical hollow body 1 illustrated in the FIGS. 1 and 2, the medical hollow body according to FIG. 3 has a piston rod 59 which is connected to the piston 5. For this, the piston rod 59 comprises a connecting area 61 which is formed in such a manner that it can be introduced into the hollow space 23 of the piston 5. At its lower end, said connecting area 61 preferably comprises a sealing means 63 which is preferably formed as radial projection circumferentially extending in the circumferential direction and tightly seals the hollow space 23 with respect to the upper subspace 7.

By means of the piston rod 59, pressure forces can be exerted on the piston 5. FIG. 3 illustrates a state of the piston 5 in which the piston is not subjected to pressure. This corresponds to the first state of the piston 5 in which no lubricant can be dispensed from the at least one receiving area 21 which is formed here by the hollow space 23. In its second state, in which lubricant can be dispensed to the at least one sliding surface 19 through the channels 25 acting as dispensing means, the piston 5 can displaced in that by means of the piston rod 59, pressure forces are introduced into the piston 5. In doing so, the piston 5 is displaced toward the connecting piece 11, thus is displaced downward. In contrast to the exemplary embodiment of the piston 5 illustrated in the FIGS. 1 and 2, the exemplary embodiment according to FIG. 3 has no diaphragm 27, but the hollow space 23 is closed with respect to the upper subspace 7 exclusively by the sealing means 63. Thus, if the piston rod 59 is displaced downward, first, the connecting area 61 with the sealing means 63 penetrates into the hollow space 23 and thus applies pressure onto the lubricant disposed in the receiving area 21. By means of said pressure, the lubricant is expelled via the channels 26 out of the hollow space 23 and is dispensed to the at least one sliding surface 19. Depending on the prevailing force conditions, the prevailing pressure in the hollow space 23 can be sufficient to effect also a displacement movement of the piston 5 toward the connection piece 11, thus in the downward direction. In this case, the pressure force introduced into the hollow space 23 and thus into the piston effects expelling the lubricant from the at least one receiving area 21 and also displacing the piston 5.

If the prevailing pressure force in the hollow space 23 is not high enough in order to effect a displacement of the piston 5, the lubricant is first completely expelled while the connecting area 61 is displaced into the hollow space 23. Once the connecting area 61 is completely arranged in the hollow space 23, the piston rod 59 abuts with a support surface 65 preferably formed as an annular shoulder against the surface 55 of the piston 5. In this case, a force can be introduced via the support surface 65 into the surface 55, which force then effects a displacement of the piston 5.

Figure 4:
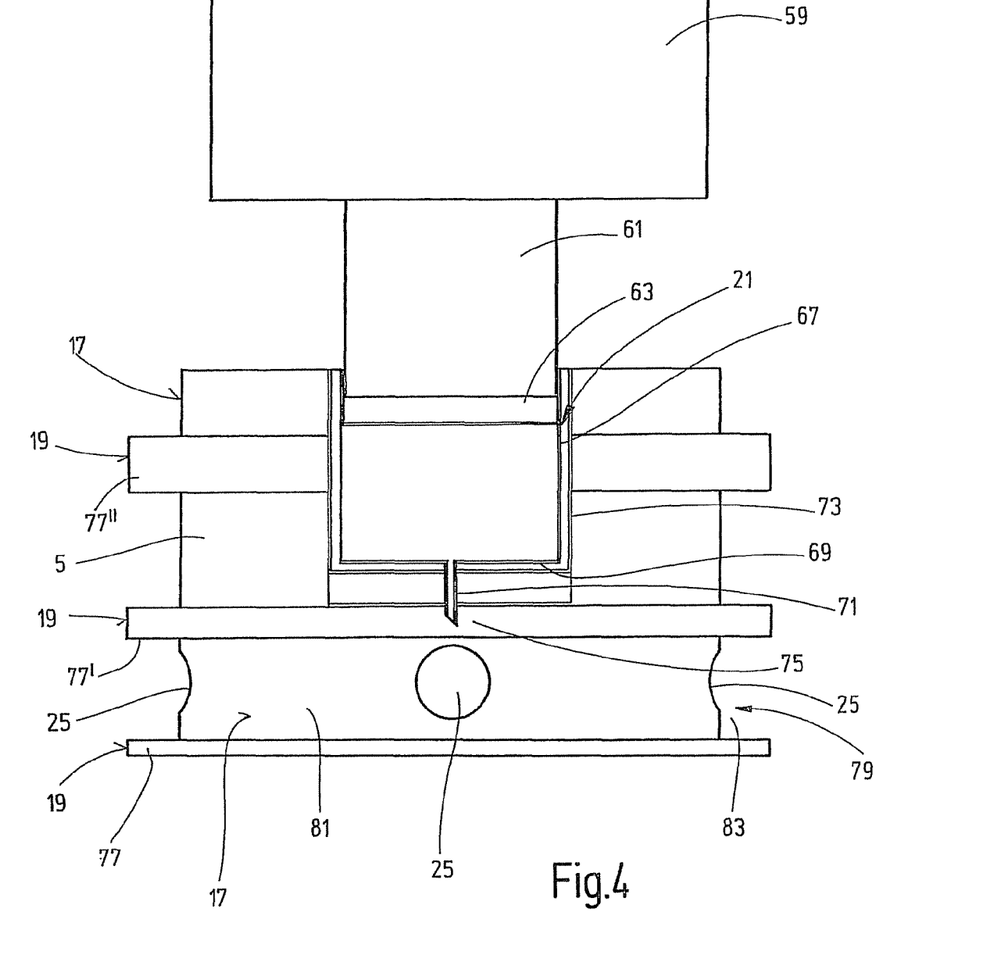
FIG. 4 shows a schematic view of a third exemplary embodiment of a piston according to claim 1 in a first functional position.

FIG. 4 shows a third exemplary embodiment of a piston 5. Identical and functionally identical elements are indicated by the same reference numbers so that in this respect, reference is made to the preceding description. In the illustrated exemplary embodiment, the at least one receiving area 21 comprises at least one reservoir 67. Said reservoir is formed here as a substantially cylindrical container which comprises a bottom 69 that has a dispensing element which is formed here as a needle 71.

In another, non-illustrated exemplary embodiment, the reservoir can comprise at least one microballoon, wherein such a microballoon has a preferably elastic sheath which encloses a lubricant volume. This sheath is formed in a tearable manner and can burst in particular upon introduction of pressure forces thereby releasing the lubricant enclosed by the sheath. Also, another exemplary embodiment is possible in which instead of a reservoir, at least one microballoon is provided. Of course, it is also possible to use more than one microballoon in connection with a reservoir or without a reservoir. In the latter case, the at least one microballoon defines the receiving area 21.

In the illustrated exemplary embodiment, the reservoir 67 is tightly sealed toward the top by a sealing means 63 of a piston rod 59. In a preferred, non-illustrated exemplary embodiment, it is possible to close the reservoir 67 by a diaphragm 27 which is elastic and/or permeable for gases.

Said reservoir 67 is arranged in a recess 73 of the piston 5 and is displaceable in the axial direction. The term "axial direction" relates here to the direction which is defined by the non-illustrated longitudinal axis of the piston 5 which coincides with the likewise not illustrated longitudinal axis of a medical hollow body 1 with which the piston 5 interacts.

In the illustrated state of the piston 5, the reservoir 67 is arranged in a first upper position in which the needle 71 does not penetrate a sealing area 75 so that no lubricant can be dispensed from the reservoir 67 downward through the needle 71 formed as a dispensing element. In this first state of the piston 5, said piston is preferably unpressurized.

On its outer surface shell 17, the illustrated piston 5 has a plurality of radial projections which extend circumferentially along its circumferential direction and the outer diameters of which are adapted in an already described manner to the inner diameter of a non-illustrated medical hollow body 1 so that a sealing effect is created and in particular at least one sliding surface 19—here, three sliding surfaces 19—are formed for contact with the hollow body 1. A first lower projection 77—viewed in the axial direction—is relatively short or thin and is in particular formed in a quasi lamella-like manner and serves substantially for sealing an area 79, in which lubricant is introduced in a second, non-illustrated state of the piston 5, with respect to the lower subspace 9 of the medical hollow body 1 so that the lubricant cannot come into contact with the substance S. In particular the projection 77 which—viewed in the axial direction—has a relative narrow, lamella-like shape, serves also for minimizing the friction acting there in the area of the at least one sliding surface 19. In the illustrated exemplary embodiment, two further projections 77', 77" are provided which—likewise viewed in the axial direction—are formed wider than the first projection 77. In particular these projections 77' and 77" serve for guiding and stabilizing the piston 5 in the interior 3 of the hollow body 1, wherein each of them comprises a sliding surface 19 for contact with the hollow body 1.

The remaining outer surface shell 17 has a diameter that is smaller than the one in the area of the projections 77, 77', 77". The area 79 is provided between the projection and the projection 77'. Said area comprises a core area 81 of the piston 5 which is enclosed by a portion of the surface shell 17 which is set back relative to the sliding surfaces 19 of the projections 77, 77'. The radial offset of the surface shell 17 results in an annular space 83 which—viewed in the circumferential direction—encompasses the core area 81 in an annular manner.

The core area 81 is penetrated by at least one channel 25 which connects a non-illustrated hollow central area of the core area 81 to the area 79, thus in particular to the annular space 83. The hollow central area is arranged below the sealing area 75 which can be pierced by the needle 71. In the present exemplary embodiment, four channels 25 are provided which—viewed in the circumferential direction—open out with the same angular partition in the annular space 83.

It is obvious that the piston 5 in FIG. 4 is illustrated in a first functional position which corresponds to the first state in which no lubricant can be dispensed from the at least one receiving area 21, thus, in this case, the reservoir 67, because the needle 41 serving as a dispensing element is closed by the sealing area 75.

Figure 5:
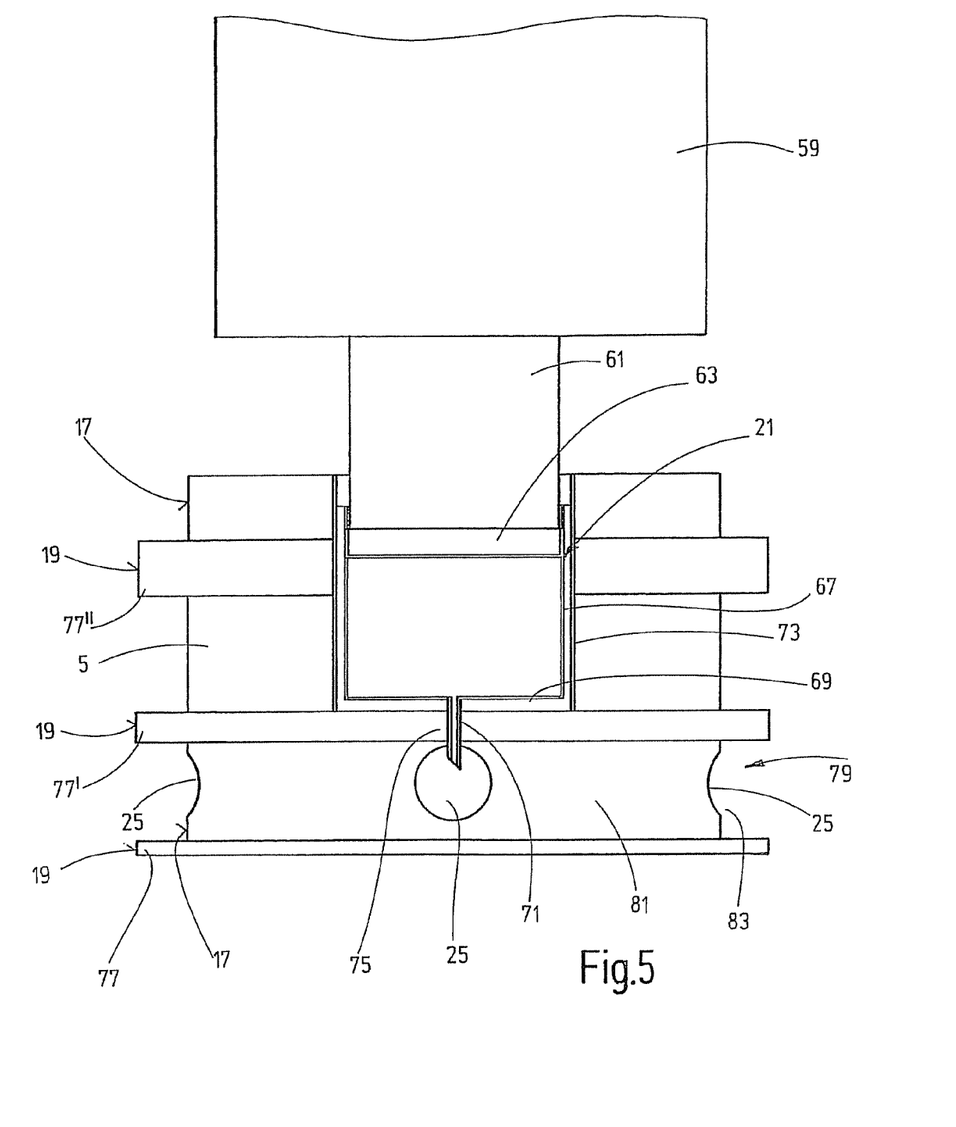
FIG. 5 shows the piston according to FIG. 4 in a second functional position.

FIG. 5 shows the piston 5 in a second functional position which corresponds to the second state in which lubricant can be dispensed from the receiving area 21, thus, in this case, the reservoir 67, to the at least one sliding surface 19. Identical and functionally identical elements are indicated by the same reference number so that in this respect, reference is made to the preceding description. It is obvious that the piston 5 in FIG. 4 is in a substantially unpressurized state. If pressure is introduced via the piston rod 59 into the reservoir 67, wherein the lubricant disposed there is pressurized, the reservoir first moves downward so that the needle 71 penetrates through the sealing area 75. FIG. 5 illustrates the state in which the needle has just pierced the sealing area 75. Thus, a fluid communication between the reservoir 67 and the non-illustrated, hollow central area of the core area 81 is established.

The following becomes clear now: The piston 5 preferably comprises a blocking device by means of which the at least one channel 25 can be blocked in the first state of the piston 5 and can be unblocked in the second state of the piston 5. In the present exemplary embodiment, the blocking device comprises the needle 71 and an area which can be pierced with the needle 71, namely the sealing area 75. In the illustrated second state of the piston 5 in which the needle 71 pierces the sealing area 75, a fluid communication between the reservoir 67 and the at least one channel 25 is established; thus, the channel 25 is unblocked.

In other exemplary embodiments, which are not illustrated, the blocking device can also comprise a predetermined breaking point, a tearable diaphragm, and/or a lip seal which is pretensioned in the blocking direction. The wording "blocking direction" addresses here that the at least one channel 25 is blocked when the lip seal is displaced in this direction. Pretensioning the lip seal in the blocking direction ensures that there is no fluid communication between the at least one receiving area and the at least one channel 25 when the piston 5 is in its first state, thus is preferably unpressurized. In the second state of the piston 5 in which the piston preferably is subjected to pressure, the needle 71, as illustrated, can pierce the piercable sealing area 75, a predetermined breaking point can break, a tearable diaphragm can tear open, and/or a lip seal pretensioned in the blocking direction can be opened by overcoming the pretension in order to unblock a fluid communication between the at least one receiving area 21 and the at least one channel 25.

Figure 6:
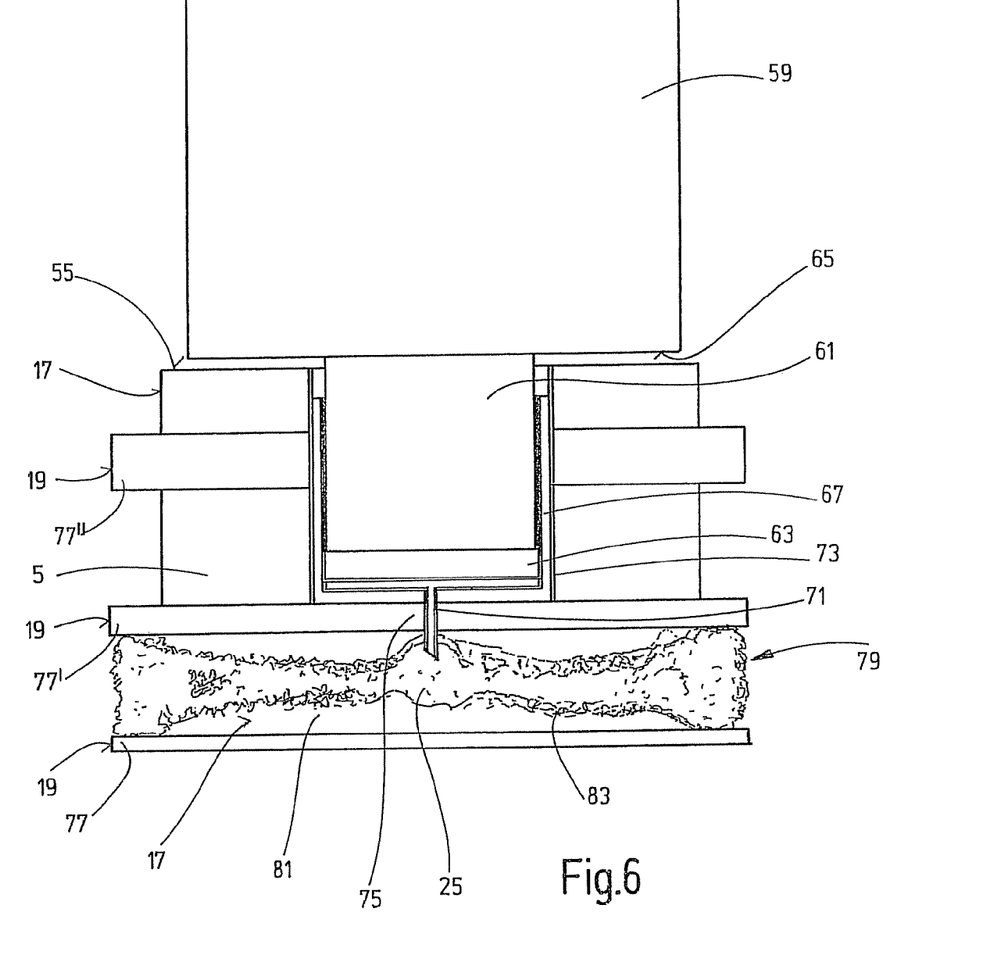
FIG. 6 shows the piston according to FIG. 4 in a third functional position.

FIG. 6 shows a third functional position of the piston 5 according to the FIGS. 4 and 5 which is also to be associated with the second state, wherein the connecting area of the piston rod 59 and the sealing means 63 are displaced farther into the reservoir 67. Identical and functionally identical elements are provided with the same reference numbers so that in this respect, reference is made to the preceding description. The displacement of the piston rod 59 and in particular of the sealing means 63 and the connecting area 61 farther downward into the reservoir 67 effects that the lubricant is expelled from the reservoir 67 via the needle 71, the hollow central area, and the at least one channel 25 into the annular space 63 and thus is dispensed to the at least one sliding surface 19. The lubricant disposed in the area 79 is indicated here by dots. Thus, in the exemplary embodiment illustrated in the FIGS. 4, 5, and 6, the at least one dispensing means which belongs to the piston 5 comprises the needle 71 formed as a dispensing element, the non-illustrated hollow central area, the at least one channel 25, and the area 79 or, respectively, the annular space 83. These elements provide a fluid communication through which the lubricant can be dispensed from the reservoir 67 to the at least one sliding surface 19.

The force exerted by the piston rod 59 on the piston 5 effects, on the one hand, that the lubricant is expelled from the reservoir 67, but, on the other, a displacement of the piston 5 also takes place. Preferably, the force relations are balanced such that during expelling the lubricant from the reservoir 67, a displacement of the piston 5 already takes place as well. However, in another exemplary embodiment it is also possible that first the lubricant is completely dispensed from the reservoir 67 to the annular space 83 before subsequently, for example by the support surface 65 abutting against the surface 55 of the piston 5, a displacement of the piston 5 takes place.

Also, the following is shown: In the case of the exemplary embodiment of a piston 5 illustrated in the FIGS. 4, 5, and 6, here too, it is not absolutely necessary that the pressure forces are introduced via a piston rod 59 into the piston 5. It is preferably also possible to close the reservoir 67 toward the top, thus toward the upper subspace 7 of a non-illustrated hollow body 1, with an elastic diaphragm and/or a diaphragm that is permeable for gases so that pressure forces can be introduced here due to a chemical reaction.

Figure 7:
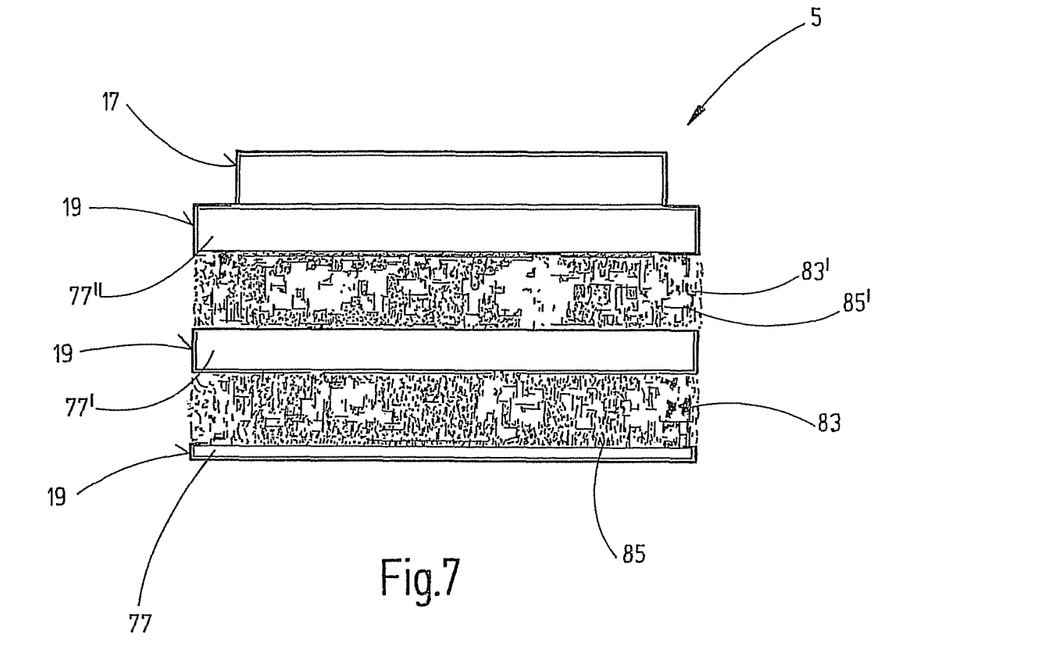
FIG. 7 shows a schematic illustration of a fourth exemplary embodiment of a piston according to claim 1.

FIG. 7 shows a fourth exemplary embodiment of a piston 5. Identical and functionally identical elements are indicated by the same reference numbers so that in this respect, reference is made to the preceding description. As the piston according to the FIGS. 4 to 6, the present exemplary embodiment too has an outer surface shell 17 from which, viewed in the circumferential direction, circumferential projections 77, 77', 77'' extend in the radial direction so that sliding surfaces 19 are formed here which have a larger outer diameter than the rest of the substantially cylindrical outer surface shell 17. Thus, here too, annular spaces 83, 83' are formed between the projections 77 and 77' and the projections 77' and 77''. Here too, the piston 5 has at least one receiving area which comprises at least one sponge, here two annularly formed sponges 85, 85', in the porous structure of which the at least one lubricant is received. The annularly formed sponges 85, 85' encompass an outer circumferential surface of the piston 5, here the outer surface shell 17, at least in certain areas.

It is obvious that in another preferred exemplary embodiment, which is not illustrated, it is also possible that a single annular space 83 with one sponge 85 is provided. In yet another exemplary embodiment, it is also possible that more than two annular spaces 83, 83' with more than two sponges 85, 85' are provided. It is also possible to divide the annular space 83 in a segment-like manner and to provide individual sponge segments in the resulting subspaces. Any other suitable arrangements are also possible. Preferably, the sponges 85, 85' have an outer diameter which is larger than the outer diameter of the piston 5 in the area of the at least one sliding surface 19. Once the piston 5 is introduced into the interior 3 of a hollow body 1, the sponges 85, 85' are compressed so that lubricant can be dispensed on their circumferential surface resting against the inner surface shell 15 of the hollow body 1. Thus, this circumferential surface serves here as a dispensing means in connection with the channels which interconnect the outer and inner pores and which are formed within the sponge. If the piston 5 is displaced within the hollow body 1, the sponges 85, 85' leave a lubricating film on the inner surface shell 15 on which the sliding surfaces 19 can slide.

It is obvious that the piston 5 according to FIG. 7 can be displaced by means of pressure forces generated by a chemical reaction as well as with the aid of a piston rod.

Figure 8:
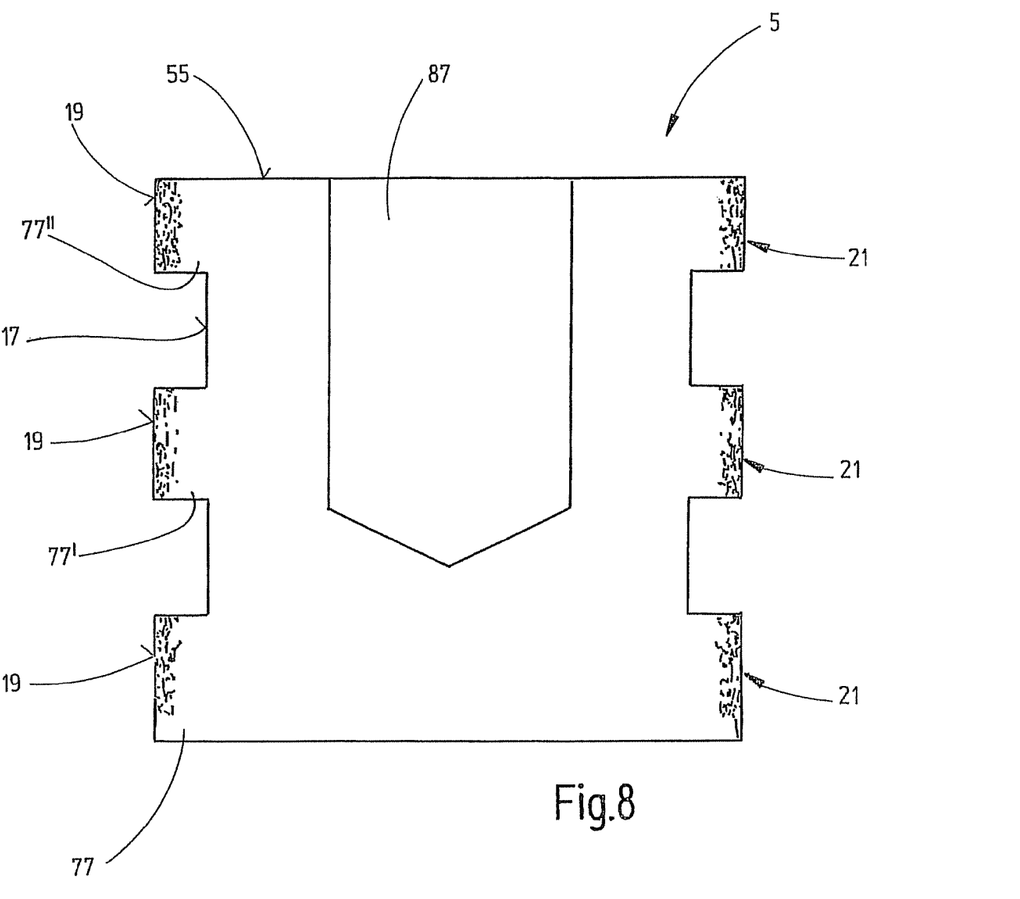
FIG. 8 shows a schematic illustration of a fifth exemplary embodiment of a piston according to claim 1.

FIG. 8 shows a fifth exemplary embodiment of a piston 5. Identical and functionally identical elements are indicated by the same reference numbers so that in this respect, reference is made to the preceding description. In this exemplary embodiment too, the outer surface shell 17 of the piston 5 has projections 77, 77', 77" which comprise sliding surfaces 19. Preferably, it is also possible to provide more than three projections 77, 77', 77". However, in another, non-illustrated exemplary embodiment, only two projections 77, 77' can be provided. Last but not least, in yet another exemplary embodiment it is possible to form the outer surface shell 17, viewed in the axial direction, with a continuous, constant diameter so that no projection 77, 77', 77" is provided and a single sliding surface 19 is formed by the entire surface shell 17.

The exemplary embodiment of a piston 5 illustrated here has receiving areas 21 which are arranged on the sliding surfaces 19 and comprise areas penetrated with microballs. These areas are illustrated here by dots. Microballs are preferably substantially spherical small capsules, wherein an outer shell encloses a hollow space in which a medium, here a lubricant, can be received. The term "microball" does not necessarily mean that these capsules have a diameter on the micrometer scale. Preferably, the microballs can have a diameter on the micrometer scale; however, exemplary embodiments with microballs having a diameter differing therefrom, in particular a larger diameter, are also preferred.

Particularly preferred, the capsules comprise the same material that is also comprised by the piston 5 in the area of the sliding surface 19. More preferably, the shell of the capsules or microballs consists of an elastomer. In the area of the sliding surface 19, the microballs filled with lubricant are preferably vulcanized into the plug material, thus are intimately connected to the same. Due to the friction forces acting during a displacement of the piston 5 on the preferably thin shell of the microballs, said microballs burst open and dispense the lubricant comprised by them to the sliding surface 19 so that a lubricating film is formed here in the contact area with the inner surface shell of the hollow body 1. Thus, the microballs themselves, which are arranged in the receiving area 21, represent the dispensing means with the aid of which, the lubricant can be dispensed from the at least one receiving area 21 to the at least one sliding surface 19.

It is obvious that also the piston 5 illustrated in FIG. 8 can be displaced by pressure forces due to a chemical reaction as well as by means of a piston rod 59. As an example, a recess 87 is indicated here in which a piston rod can engage. However, it is also possible to introduce reaction gases into the recess 87 so that pressure forces act not only on the surface 55 of the piston 5, but act also in the recess 87 due to the reaction gases, which finally results in a displacement of the piston 5.

Figure 9:
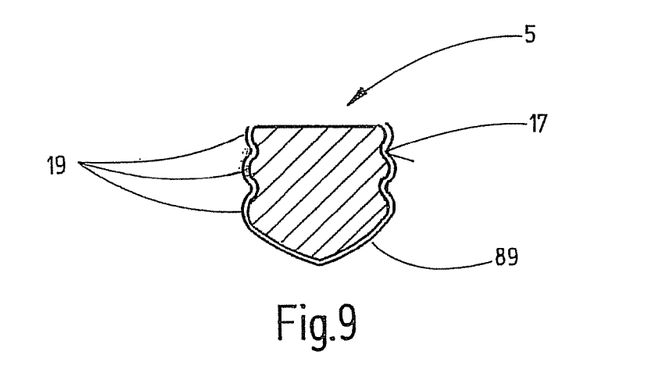
FIG. 9 shows a schematic illustration of an exemplary embodiment of a piston according to claim 14.

FIG. 9 shows an exemplary embodiment of a piston 5 which has no receiving area for a lubricant and no dispensing means. Said piston comprises a substantially cylindrical outer surface shell 17 which—viewed in cross-section—is formed in a wave-shaped manner. Thus, three subsurfaces of the surface shell 17 form sliding surfaces 19 for contact with the hollow body 1, as already explained in connection with FIG. 1. The illustrated exemplary embodiment of the piston 5 comprises, at least in the area of the at least one sliding surface 19, a smooth nonpolar material. Preferably, said smooth nonpolar material comprises PTFE and, particularly preferred, consists of PTFE which is better known under the trade name Teflon. This material has particularly low static friction and sliding friction coefficients, whereby the friction forces between the at least one sliding surface 19 and the inner surface shell 15 of a hollow body 1, which is not illustrated here, can be significantly reduced. In this manner it is possible to displace the piston 5 in the hollow body 1 while completely eliminating a lubricant. In this case too, such a displacement can of course be carried out by pressure forces formed due to a chemical reaction, but also with the aid of a piston rod 59.

Preferably, the piston 5 is coated at least in the area of the at least one sliding surface 19 with a film 89 which comprises PTFE and preferably consists of PTFE.

In another, non-illustrated exemplary embodiment, the piston 5 consists of PTFE. In this case too, the friction between the at least one sliding surface 19 and the inner surface shell 15 of a hollow body 1 is significantly reduced.

Overall, it becomes apparent that all described exemplary embodiments of a piston 5 and a medical hollow body 1 have in common that a coating of the inner surface shell 15 of the hollow body 1 can be dispensed with in an advantageous manner, at least prior to a usage of said surface shell. In this manner it can be excluded that primarily during storage, but preferred also during the use of the hollow body 1, a pharmaceutical substance S disposed in the interior 3 of the hollow body 1 comes into contact with lubricant, in particular silicone, silicone oil, and/or silicone oil emulsion, whereby instability of the pharmaceutical substance S, in particular aggregate formation and/or precipitation can be avoided. Hereby, it is in particular also possible to avoid undesirable immune reactions in a patient into whom the pharmaceutical substance S is injected. Furthermore, burdening the organism of the patient with lubricant injected together the pharmaceutical substance S is excluded.

The invention claimed is:

1. A medical dispensing device comprising:
   a hollow body;
   a piston disposed in the hollow body and defining at least one receiving area, the piston including at least one sliding surface in contact with the hollow body, the piston including at least one radially extending channel, the piston disposed between an upper subspace and a lower subspace of the hollow body;
   a lubricant disposed in the at least one receiving area; and
   at least one diaphragm which closes the at least one receiving area at least in certain areas;
   a device for pressurizing the upper subspace such that pressure in the upper subspace dispenses lubricant through the at least one radially extending channel to the at least one sliding surface and pressure in the upper subspace further translates the piston within the hollow body;
   wherein the medical dispensing device is selected from a group consisting of a syringe and a carpule.

2. The medical dispensing device of claim 1, wherein the diaphragm is operable in a first state and a second state such that in the first state lubricant is prevented from dispersion from the at least one receiving area and in the second state lubricant is dispersed from the at least one receiving area, through the at least one radially extending channel and to the at least one sliding surface.

3. The medical dispensing device of claim 1, wherein the device for pressurizing the upper subspace exerts a pressure on the piston in response to a chemical reaction.

4. The medical dispensing device of claim 3, wherein the device for pressurizing the upper subspace includes first and second channels for reacting to create the pressure.

5. A piston for a medical hollow body, the piston comprising:
- at least one sliding surface for contact with the hollow body;
- at least one receiving area arranged within the piston and containing a lubricant, the at least one receiving area in selective communication with the at least one sliding surface;
- a sealing area; and
- a needle;
- wherein the piston is operative in a first state and a second state such that in the first state, communication between the at least one receiving area and the at least one sliding surface is prevented, and in the second state, the at least one receiving area is in communication with the at least one sliding surface to dispose lubricant to the at least one sliding surface and the needle penetrates the sealing area.

6. A piston for a medical hollow body, the piston comprising:
- at least one sliding surface for contact with the hollow body; and
- a microballoon having a sheath defining at least one receiving area and containing a lubricant, the at least one receiving area in selective communication with the at least one sliding surface;
- wherein the piston is operative in a first state and a second state such that in the first state, communication between the at least one receiving area and the at least one sliding surface is prevented, and in the second state, the at least one receiving area is in communication with the at least one sliding surface to dispose lubricant to the at least one sliding surface,
- wherein the sheath is torn in the second state.

* * * * *